(12) United States Patent
Kainosho et al.

(10) Patent No.: US 8,022,173 B2
(45) Date of Patent: Sep. 20, 2011

(54) STABLE ISOTOPE-LABELED ALIPHATIC AMINO ACIDS, METHOD FOR INCORPORATING THE SAME IN TARGET PROTEIN AND METHOD FOR NMR-STRUCTURAL ANALYSIS OF PROTEINS

(75) Inventors: Masatsune Kainosho, Tokyo (JP); Tsutomu Terauchi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/198,462

(22) Filed: Aug. 26, 2008

(65) Prior Publication Data
US 2009/0075388 A1 Mar. 19, 2009

Related U.S. Application Data

(63) Continuation of application No. PCT/JP2007/053593, filed on Feb. 27, 2007.

(30) Foreign Application Priority Data

Feb. 27, 2006 (JP) .................................. 2006-050926

(51) Int. Cl.
*C07K 14/00* (2006.01)
*C07C 229/00* (2006.01)
(52) U.S. Cl. ......... 530/300; 562/443; 562/445; 562/553
(58) Field of Classification Search .................. None
See application file for complete search history.

(56) References Cited

U.S. PATENT DOCUMENTS
2005/0084452 A1* 4/2005 Kainosho et al. ............ 424/9.34

FOREIGN PATENT DOCUMENTS
| EP | 1 457 482 A1 | 9/2004 |
| EP | 1 679 302 A1 | 7/2006 |
| WO | 03053910 A1 | 7/2003 |
| WO | 2005042469 A1 | 5/2005 |

OTHER PUBLICATIONS

Coggins et al (Nature Structural Biology, Structure of the LpxC deacetylase With a Bound Substrate-Analog Inhibitor, 10(8), pp. 645-651.*
Kainosho et al., Optimal isotope labelling for NMR protein structure determinations; Nature, vol. 440, No. 7080, pp. 52-57, Mar. 2, 2006.
Tugarinov et al.; Solution NMR-derived global fold of a monmeric 82-kDa enzyme, Proc. Natl. Acad. Sci., vol. 102, No. 3, pp. 622-627, 2005.
Wuthrich, NMR Spectra of Proteins and Nucleic Acids in Solution; Wiley, New York, 1991, pp. 26-31.
Wuthrich, K., "Chapter 4, The NMR Assignment Problem in Biopolymers", Willey, New York, pp. 42-43, (1991).
Examination report for German Patent Application No. 11 2007 000 484.3-44, dated Nov. 12, 2010.

* cited by examiner

*Primary Examiner* — Paul A Zucker
(74) *Attorney, Agent, or Firm* — Hoffmann & Baron, LLP

(57) ABSTRACT

The present invention herein provides a combination of stable isotope-labeled aliphatic amino acids, which permits the structural analysis of a high molecular weight protein, in particular, a high molecular weight protein whose molecular weight exceeds 60 kDa. This is a combination of stable isotope-labeled amino acids which is characterized in that arginine (Arg), glutamine (Gln), glutamic acid (Glu), lysine (Lys), methionine (Met) and proline (Pro) satisfy the following requirements concerning the labelling pattern:
(b) one of the methylene hydrogen atoms of at least one of the methylene groups is deuterated and the both of the two methylene hydrogen atoms of at least one of the methylene groups are likewise deuterated; and
(d) when they each have a methyl group, the hydrogen atoms of the methyl group except for one of the same are deuterated, or the methyl group is completely deuterated.

12 Claims, 7 Drawing Sheets

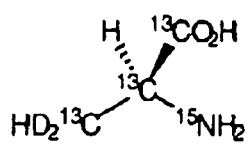
Ah
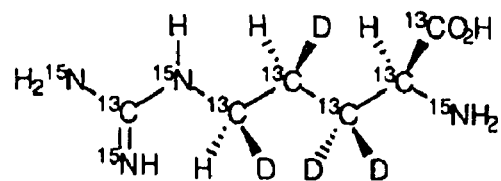
Arg
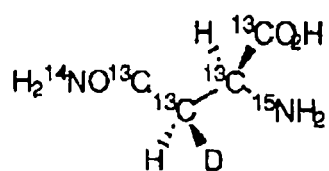
Asn
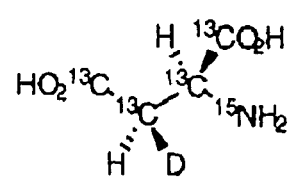
Asp
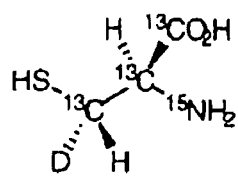
Cys
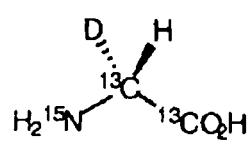
Gly
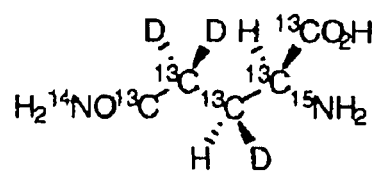
Gh
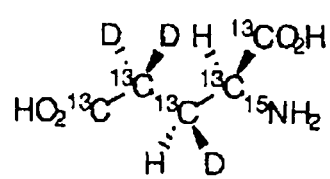
Glu
FIG. 2-1

STABLE ISOTOPE-LABELED ALIPHATIC AMINO ACIDS, METHOD FOR INCORPORATING THE SAME IN TARGET PROTEIN AND METHOD FOR NMR-STRUCTURAL ANALYSIS OF PROTEINS

CROSS-REFERENCE TO RELATED APPLICATIONS

This application is a continuation of International Application No. PCT/JP2007/053593, filed Feb. 27, 2007, which claims priority to Japanese Patent Application No. 2006-50926, filed Feb. 27, 2006, the contents of each of which are incorporated herein by reference.

TECHNICAL FIELD

The present invention relates to a stable isotope-labeled aliphatic amino acid useful in the protein structure analysis by NMR, a method for the incorporation of the amino acid into a target protein and a method for the structural analysis of a protein through the NMR technique.

BACKGROUND ART

The NMR technique is presently the only technique which permits the observation of the three-dimensional structure of a protein present in a solution and of the movement or activity thereof at a resolution of atomic level. The studies based on the three-dimensional structures of proteins have recently widely been made not only in the fields of the basic research institutions such as those belonging to various universities, but also in the industrial fields including the recent drug-preparation industries. However, the NMR spectrometry is a novel technique developed only about 20 years ago and therefore, it would involve a number of obstructions (problems) to be overcome in the near future. One of such problems is that the NMR spectrometry is limited in the molecular weight of a subject to be analyzed (Non-Patent Document 1).

In the NMR analysis, the increase in the molecular weight of a protein whose structure should be elucidated results in any possible overlapping between NMR signals caused by an increase in the number of signals and any reduction of signal intensities due to the rapid relaxation phenomenon. In particular, if the molecular weight of a target protein exceeds about 20,000, it would be essential to the elimination of any error accompanied by this technique to develop a more precise and advanced NMR technique.

The structural analysis technique which makes use of a highly stable isotope-labeled protein "Stereo-Array Isotope-Labeling technique (SAIL Technique)" is a method wherein any unnecessary structural information obtained in the $^1$H-NMR analysis is eliminated except for that needed and sufficient for the NMR structural analysis through the exhaustive and selective deuteration of a target protein (SAIL protein) to thus permit the considerable reduction of the time required for the NMR measurement and/or analysis. The methods disclosed in Patent Documents 1 and 2 are techniques which not only allow the highly precise structural elucidation of a target protein, but also permit the automatic structural analysis, with high precision, of even a protein having a molecular weight of about 40,000 higher than the aforementioned upper limit thereof. Thus, there has hereafter been desired for the development of a novel technique which may allow the automatic analysis of fine and precise structure of a high molecular weight protein or a membrane protein, which has a molecular weight of not less than 60 kDa.

In the SAIL technique, the sensitivity of residual signal of a protein is further improved and the limit in the molecular weight of a protein to be analyzed is expanded from the conventional level on the order of 30 kDa to not less than 40 kDa through the efficient increase in the deuteration density of such protein (Non-Patent Document 2). However, the structural analysis of a protein whose molecular weight exceeds 60 kDa cannot easily be analyzed by any simple application of the conventional SAIL amino acids, because of an increase in the signal line width caused by the reduction in the mobility of the protein molecule and of any possible overlapping between NMR signals due to an increase in the number of signals. Moreover, the membrane protein is dissolved in an appropriate medium in the presence of lipids or a detergent, although the molecular weight of the protein per se is not high and therefore, the substantial molecular weight of the membrane protein becomes high and this in turn results in the reduction of the mobility of the protein molecule. Accordingly, the analysis of such a membrane protein through the use of the NMR is not easy like the NMR analysis of the high molecular weight protein. From the aforementioned reasons, there has been desired for the development of any means for obtaining structural information of membrane proteins and high molecular weight proteins, which may presently become subjects for the development of pharmaceutical agents.

Patent Document 1: International Patent Publication WO 03/053910A1;
Patent Document 2: International Patent Publication WO 2005/042469A1;
Non-Patent Document 1: Wuthrich K (1986), NMR of proteins and nucleic acids, Wiley, New York, Wuthrich K (1991); Structural Analysis of Proteins and Nucleic Acid According to the NMR-Two-Dimensional NMR Spectroscopy, Tokyo Kagaku-Dojin Publishing Co., Ltd.;
Non-Patent Document 2: Kainosho M, Torizawa T, Iwashita Y, Terauchi T, Ono M, Guntert P. Nature 2006; in press.

DISCLOSURE OF THE INVENTION

It is an object of the present invention to provide a combination of stable isotope-labeled aliphatic amino acids, which permits the structural analysis of a high molecular weight protein, in particular, one having a molecular weight exceeding 60 kDa.

It is another object of the present invention to provide a combination of stable isotope-labeled amino acids, which permits the structural analysis of a high molecular weight protein.

It is a further object of the present invention to provide a method for the incorporation of such a stable isotope-labeled amino acid into a target protein.

It is a still further object of the present invention to provide a method for preparing a target protein which is composed of stable isotope-labeled amino acid.

It is still another object of the present invention to provide an NMR method for elucidating the structure of a protein, in which the NMR spectroscopy can ensure a further improved sensitivity.

The inventors of this invention have conducted various studies to accomplish the foregoing objects, have found that any possible overlapping between NMR signals encountered when a protein is subjected to the NMR analysis can significantly be reduced as compared with that observed for the foregoing conventional techniques to thus effectively solve the foregoing problems, when using, as a stable isotope-labeled aliphatic amino acid component, the stable isotope-labeled aliphatic amino acid which is disclosed in Patent Document 1 and has at least two methylene groups each carrying two hydrogen atoms, wherein one of the methylene hydrogen atoms of at least one of the methylene groups present on the aliphatic amino acid is deuterated (partially deuterated) and the both of the two methylene hydrogen atoms of at least one of the methylene groups present thereon are likewise deuterated (completely deuterated), and have thus completed the present invention on the basis of the foregoing finding.

Accordingly, the present invention herein provides a combination of stable isotope-labeled amino acids in which all of the aliphatic amino acids constituting a target protein satisfy the following requirements concerning the labelling pattern:
(a) When only one methylene group carrying two hydrogen atoms exists, one of the methylene hydrogen atoms is deuterated;
(b) When at least two methylene groups each carrying two hydrogen atoms exist, one of the methylene hydrogen atoms of at least one of the methylene groups is deuterated and the both of the two methylene hydrogen atoms of at least one of the methylene groups are likewise deuterated;
(c) When pro-chiral gem-methyl groups exist, all of the hydrogen atoms on one of the methyl groups are completely deuterated while the hydrogen atoms on the other methyl groups are partially deuterated;
(d) When a further methyl group in addition to the foregoing ones exist, the hydrogen atoms except for one of the same are deuterated, or the methyl group is completely deuterated; and
(e) The methine hydrogen atoms are deuterated.

The present invention also provides a combination of stable isotope-labeled amino acids in which arginine (Arg), glutamine (Gln), glutamic acid (Glu), lysine (Lys), methionine (Met) and proline (Pro) satisfy the following requirements concerning the labelling pattern:
(b) one of the methylene hydrogen atoms of at least one of the methylene groups is deuterated and the both of the two methylene hydrogen atoms of at least one of the methylene groups are likewise deuterated; and
(d) when the amino acid moiety has a methyl group, the hydrogen atoms except for one of the same are deuterated, or the methyl group is completely deuterated.

The present invention likewise provides a combination of stable isotope-labeled amino acids constituting a target protein in which the aliphatic amino acids constituting the target protein are the foregoing stable isotope-labeled aliphatic amino acids and the aromatic amino acids constituting the protein are stable isotope-labeled aromatic amino acids selected from those listed below:

A stable isotope-labeled phenylalanine, in which the carbon atom of a phenyl group attached to an amino acid residue represented by the following formula A is $^{13}C$ atom; 2 to 4 carbon atoms out of the remaining 5 carbon atoms constituting the phenyl group are $^{12}C$ atoms, each of which is combined with a deuterium; and the remaining carbon atoms of the phenyl group are $^{13}C$ atoms, each of which is combined with a hydrogen atom;

A stable isotope-labeled tyrosine, in which the carbon atom of a phenyl group attached to an amino acid residue represented by the following formula A is $^{13}C$ atom; the carbon atom combined with the hydroxyl group (OH group) present on the phenyl group is a $^{12}C$ atom or a $^{13}C$ atom; 2 to 4 carbon atoms out of the remaining 4 carbon atoms constituting the phenyl group are $^{12}C$ atoms, each of which is combined with a deuterium; and the remaining carbon atoms of the phenyl group are $^{13}C$ atoms, each of which is combined with a hydrogen atom;

A stable isotope-labeled tryptophane, in which the carbon atom of an indolyl group attached to an amino acid residue represented by the following formula A is $^{13}C$ atom; 1 to 5 carbon atoms out of the remaining 7 carbon atoms constituting the indolyl group are $^{12}C$ atoms, each of which is combined with a deuterium; the remaining carbon atoms of the indolyl group are $^{13}C$ atoms, each of which is combined with a hydrogen atom; and the nitrogen atom of the NH group constituting the indolyl group is a $^{15}N$ atom or a $^{14}N$ atom; and A stable isotope-labeled histidine, in which the carbon atom of an imidazolyl group attached to an amino acid residue represented by the following formula A is $^{13}C$ atom; the both of the remaining 2 carbon atoms constituting the imidazolyl group are $^{13}C$ atoms, which are each combined with a hydrogen atom, or one of the carbon atoms is a $^{13}C$ atom which is combined with a deuterium and the other carbon atom is a $^{13}C$ atom which is combined with a hydrogen atom; one of the two nitrogen atoms constituting the imidazolyl group is a $^{15}N$ atom and the other thereof is a $^{14}N$ atom; and the hydrogen atom constituting the NH group is not a deuterium:

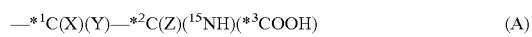

$$—*^{1}C(X)(Y)—*^{2}C(Z)(^{15}NH)(*^{3}COOH) \qquad (A)$$

wherein each of $*^{1}C$, $*^{2}C$, and $*^{3}C$ represents a $^{12}C$ or $^{13}C$ atom; X, Y and Z each represent a hydrogen atom or a deuterium atom.

According to the present invention, there is also provided a method for the incorporation of the foregoing stable isotope-labeled amino acids into a target protein, which comprises the step of cultivating microorganisms or animal or plant cells using a culture medium to which the foregoing amino acids are incorporated to thus integrate a gene coding for a target protein into the microorganisms or animal or plant cells.

According to the present invention, there is further provided a method for the synthesis of a target protein which comprises the step of synthesizing the target protein according to the chemical synthesis technique while using a combination of stable isotope-labeled aliphatic amino acids as the whole amino acid components constituting the target protein.

According to the present invention, there is likewise provided an NMR method for elucidating the structure of a protein, which comprises the steps of incorporating the aforementioned stable isotope-labeled aliphatic amino acids into a target protein and then subjecting the target protein to the NMR analysis to thus elucidate the structure of the protein.

The present invention thus permits the achievement of the following effects:
(i) The present invention is deprived of a part of the quantities of NMR information required for the precise elucidation of the structure of a protein due to the deuteration of a protein to be analyzed. However, the lost NMR signals would be those undergoing overlapping with the signals of other atomic groups with a high probability while they are investigated on the basis of the data base and the lost NMR signals are so selected that the structural information can, in most cases, be supplemented while taking into consideration the structural information of the neighboring atomic groups. Accordingly, the present invention would permit the correct elucidation of the three-dimensional structure of a high molecular weight protein having a molecular weight of higher than 50 kDa. In this respect, the conventional SAIL method cannot easily be applied to such a high molecular weight protein without any modification.

(ii) The present invention would also permit the correct elucidation of the three-dimensional structure of a membrane protein.

BRIEF DESCRIPTION OF THE DRAWINGS

FIG. 2-1 shows the chemical structures of representative stable isotope-labeled amino acids.

FIG. 2-2 shows the chemical structures of representative stable isotope-labeled amino acids (continued from FIG. 2-1).

FIG. 2-3 shows the chemical structures of representative stable isotope-labeled amino acids (continued from FIG. 2-1).

FIG. 3 shows the structure of calmodulin protein whose structure is elucidated according to the conventional SAIL method (experimental data) or elucidated using the amino acids of the present invention (data obtained through the simulation experiments). (A): The structure elucidated according to the SAIL method (ribbon model); (B): the structure elucidated according to the SAIL method (bundle model); and (C): the structure elucidated using the amino acids of the present invention.

BEST MODE FOR CARRYING OUT THE INVENTION

In the present invention, the stable isotope-labeled aliphatic amino acids satisfying the foregoing requirements (a), (c), (d) and (e) can be prepared by the method disclosed in Patent Document 1. It is herein contemplated that the whole content of Patent Document 1 is incorporated into the description of this specification.

The amino acids which satisfy the foregoing requirements (b) and (d) or arginine (Arg), glutamine (Gln), glutamic acid (Glu), lysine (Lys), methionine (Met) and proline (Pro) can easily be synthesized according to the method as will be described in Examples of this specification.

The stable isotope-labeled aromatic amino acids represented by the foregoing formula A can be prepared by the method disclosed in Patent Document 2. It is herein contemplated that the whole content of Patent Document 2 is incorporated into the description of this specification.

Figure 1:
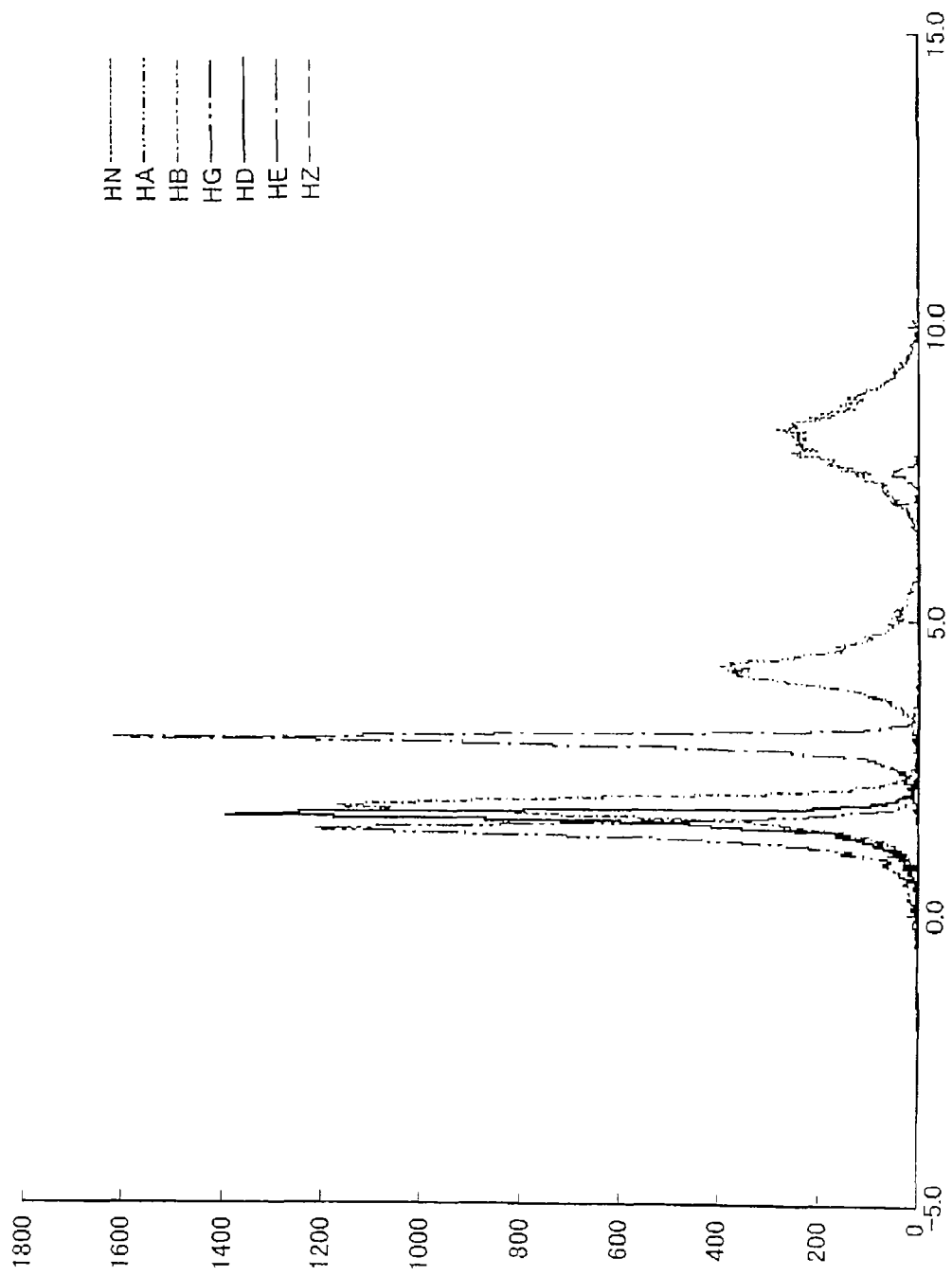
FIG. 1 shows the chemical shift distribution of each atom present in a lysine residue obtained by searching for the BMRB data base. In this figure, the chemical shift is plotted as abscissa and the frequency of each atom concerned appearing in the data base as ordinate.

The amino acids which satisfy the foregoing requirements (b) and (d) or arginine (Arg), glutamine (Gln), glutamic acid (Glu), lysine (Lys), methionine (Met) and proline (Pro) as well as stable isotope-labeled isoleucine (Ile), valine (Val), threonine (Thr), or leucine (Leu) will now be described in detail below:

The chemical shift distribution observed for each atom present in a lysine residue while referring to the BMRB data base (http://www.bmrb.wisc.edu/) reference from (Seavey B R, Farr E A, Westler W M, Markley J L., J. Biomol. NMR, 1991, 1: 217-236) is depicted on FIG. 1 by way of example. Regarding this figure, the chemical shift is plotted as abscissa, while the frequency of the atomic group concerned appearing in the data base is plotted as ordinate. As will be seen from these results, the chemical shifts of β-, γ- and δ-protons of lysine are very close to one another (see FIG. 1) and the attribution of these shifts is rarely quite difficult due to the overlapping between them even in case of SAIL proteins. Accordingly, it is rather preferred to subject, to regio-selective $CD_2$ labelling (complete deuteration), methylene protons present on the side chains of a long chain amino acid such as lysine and arginine. This labelling method leads to an increase of the rate of deuteration, and this in turn results in a decrease of the total number of signals, but the method can provide the NMR spectroscopic information concerning at least one of the methylene protons. Therefore, accuracy and precision of the structure of a target protein would rather be improved. In fact, it has been proved, by the present invention, that the approximate three-dimensional structures of an amino acid residue and the side chain thereof can be elucidated in the light of the results obtained according to simulation experiments, if the positional information of protons situating at least one position on the side chain of an amino acid residue can be obtained. In addition, the nuclei of the α- and β-hydrogen atoms are preferably $^1H$ in order to determine the precise folded structure of a protein and it has also been proved that the nuclei of the hydrogen atoms at the terminal of the side chain on an amino acid residue are likewise preferably $^1H$ to precisely determine the overall structure of the side chain on a long chain amino acid residue even to the terminal thereof.

With regard to the methine protons of a branched amino acid, it is demonstrated, by the conventional method, that the signal intensities of methine protons are weak and it is, accordingly, predicted that, in most cases, the signals thereof are not observed in case of high molecular weight proteins. For this reason, the methine protons are deuterated to thus improve the rate of deuteration.

Moreover, when labelling carbon atoms of an amino acid, the carbon atoms completely deuterated are preferably replaced with $^{13}C$ atoms and/or $^{12}C$ atoms, but they are more preferably $^{12}C$ atoms, while taking notice of the optimization of the relaxation of the neighboring $^1H$ atoms.

After the completion of the deuteration, it is preferred that all of the carbon atoms of methylene groups and/or methyl groups each carrying hydrogen atoms are replaced with $^{13}C$ atoms.

In addition, all of the carbon atoms constituting a specific amino acid are preferably $^{13}C$ atoms and one of the hydrogen atoms present on the β-methylene group is preferably deuterated.

Moreover, it is preferred that the nitrogen atoms constituting an amino acid are completely or partially replaced with $^{15}N$ atoms.

Preferably used herein as the stable isotope-labeled aliphatic amino acids include, for instance, those represented by the following formulas (1) to (13):

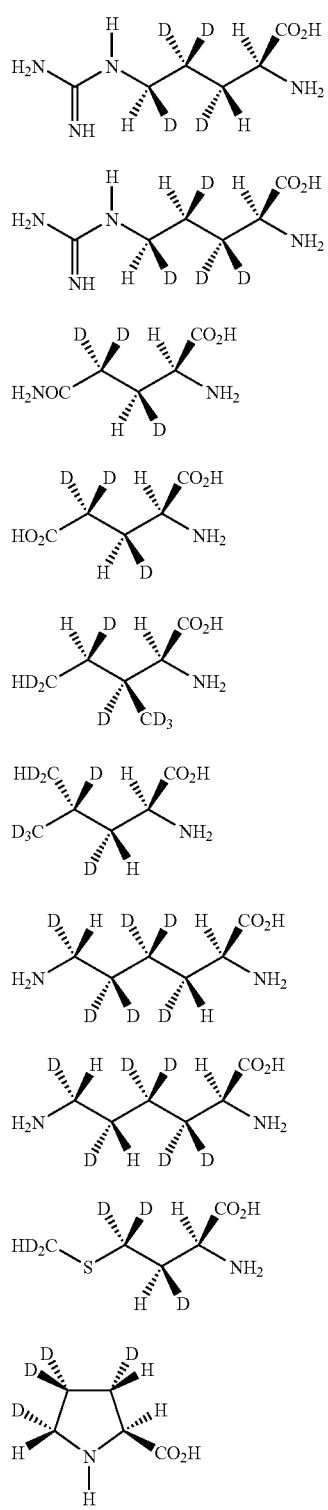

[Chemical Formula 1]
[Chemical Formula 2]
[Chemical Formula 3]
[Chemical Formula 4]
[Chemical Formula 5]
[Chemical Formula 6]
[Chemical Formula 7]
[Chemical Formula 8]
[Chemical Formula 9]
[Chemical Formula 10]

-continued

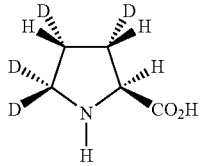

[Chemical Formula 11]

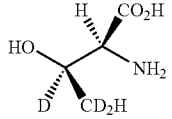

[Chemical Formula 12]

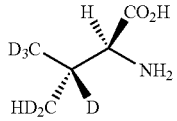

[Chemical Formula 13]

Wherein, in these formulas, the carbon atoms included therein are $^{12}C$ or $^{13}C$ atoms; the nitrogen atoms present therein are $^{14}N$ or $^{15}N$ atoms; H represents a hydrogen atom; and D represents a deuterium atom.

The following are the most preferred labelling patterns for arginine (Arg), glutamine (Gln), glutamic acid (Glu), isoleucine (Ile), leucine (Leu), lysine (Lys), methionine (Met), proline (Pro), threonine (Thr) and valine (Val). In this respect, however, the configuration of the side chain-stereoselective stable isotope labels is not particularly specified in the following labelling patterns and it may be either R or S configuration.

Arg:

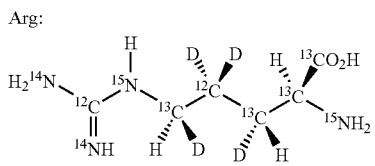

In this amino acid, the hydrogen atom situating at the β-position gives important information on distances for the determination of the three-dimensional structure of a protein and therefore, it is preferred that the hydrogen atom is stereoselectively labelled with a deuterium atom.

The hydrogen atom situating at the γ-position and that situating at the β-position may overlap one another at a high probability and accordingly it is preferred that the hydrogen atom at the γ-position is completely deuterated in order to make the attribution or identification of the hydrogen atom at the β-position easy. Furthermore, the carbon atom at the γ-position which never provides any information on the proton is preferably $^{12}C$ atom.

The hydrogen atom situating at the δ-position is effective for the determination of the conformation of the side chain on an arginine residue and for this reason, it is preferably stereoselectively labelled with a deuterium atom.

The guanidino group may be or may not be subjected to isotope-labelling.

Gln, Glu:

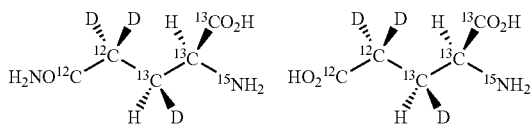

The hydrogen atom situating at the β-position gives important information on distances for the determination of the three-dimensional structure of a protein and therefore, it is preferably labelled with a stereo-selective deuterium atom.

In these amino acids, it is preferred that the hydrogen atom situating at the γ-position is completely deuterated in order to prevent the occurrence of any overlapping with other hydrogen atoms and to make the signal ascribable to the neighboring hydrogen atoms more sharp. In addition, the hydrogen atom at the γ-position is preferably $^{12}C$ atom.

When it is desired to precisely obtain the three-dimensional structure in the proximity to the carbon atom at the γ-position, preferably used herein as a label is one having a $^{13}CHD$ group at the γ-position. In this case, the atomic group at the β-position may be any one selected from either $^{13}CD_2$ or $^{12}CD_2$; the carbon atom at the δ-position may be $^{12}C$ or $^{13}C$; and the nitrogen atom at the ε-position may be either $^{14}N$ or $^{15}N$.

Ile:

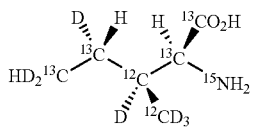

The signals ascribable to the hydrogen atom situating at the β-position can frequently be observed with great difficulties due to an increase in the line widths of signals. However, the signals attributable to this hydrogen atom may be eliminated through the deuteration thereof. This is because the loss of the information associated with the deuteration of the hydrogen atom at the β-position can be compensated using the information on the signals ascribable to $^{13}CD_2H$ at the $γ_2$-position or/and to $^{13}CHD$ at the $γ_1$-position inasmuch as one can obtain the information on the position of the methyl group at the $γ_2$-position, while taking notice of the tetrahedral characteristic properties of the carbon atom at the β-position.

In any case, the carbon atom carrying only deuterium atoms is preferably a $^{12}C$ atom.

The methyl group at the δ-position is preferably labelled to give a group: $^{13}CD_2H$.

Leu:

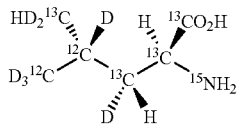

In this amino acid, it is preferred that the methylene group at the β-position is stereo-selectively labelled with a deuterium atom.

The carbon atom carrying only deuterium atoms is preferably a $^{12}C$ atom.

The signals ascribable to the hydrogen atom situating at the γ-position can frequently be observed with great difficulties due to an increase in the line widths of signals. However, the signals attributable to this hydrogen atom may be eliminated through the deuteration thereof. This is because the precision of the three-dimensional structure-elucidation can be ensured if one can obtain the information on the position about one of the two methyl groups present at the δ-position, while taking into consideration the tetrahedral characteristic properties of the carbon atom at the β-position.

In the present invention, it is preferred that one of the two methyl groups present at the δ-position is labelled to give a $^{12}CD_3$ group and the other methyl group is labelled to give a $^{13}CD_2H$ group.

Lys:

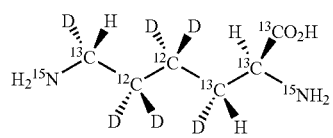

In this amino acid, the hydrogen atom situating at the β-position gives important information on distances effective for the determination of the three-dimensional structure of a protein and therefore, it is preferred that the hydrogen atom is stereo-selectively labelled with a deuterium atom.

The signals ascribable to the hydrogen atoms situating at the γ- and δ-positions may be superimposed with that ascribable to the hydrogen atom situating at the β-position with a high probability and accordingly, it is preferred that the hydrogen atoms at the γ- and δ-positions are completely deuterated in order to make the attribution or identification of the hydrogen atom at the β-position easy. Furthermore, the carbon atoms at the γ- and δ-positions which never provide any information on the proton are preferably $^{12}C$ atoms.

The hydrogen atom situating at the ε-position is effective for the determination of the conformation of the side chain on a lysine residue and therefore, it is preferably stereo-selectively labelled with a deuterium atom.

Met:

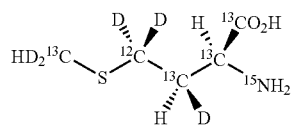

In this amino acid, the hydrogen atom situating at the β-position gives important information on distances effective for the determination of the three-dimensional structure of a protein and therefore, it is preferably stereo-selectively labelled with a deuterium atom.

It is preferred that the hydrogen atom at the γ-position is completely deuterated in order to prevent the occurrence of any overlapping between the signals ascribable to this hydrogen atom and those ascribable to other hydrogen atoms and to make the signals attributable to the hydrogen atoms in the proximity to the former more sharp. Furthermore, the carbon atom at the β-position is preferably a $^{12}C$ atom.

The hydrogen atom situating at the ε-position is effective for the determination of the conformation of the side chain attached to a methionine residue and therefore, it is preferably labelled with a deuterium atom to give a $^{13}CD_2H$ group.

Pro:

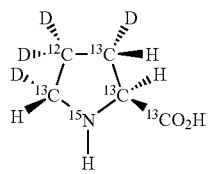

In this amino acid, the hydrogen atoms situating at the β- and δ-position give important information on distances effective for the determination of the three-dimensional structure of a protein and therefore, they are preferably stereo-selectively labelled with deuterium atoms.

It is preferred that the hydrogen atom at the γ-position is completely deuterated in order to make the attribution of other hydrogen atoms easy, since the signals ascribable to the hydrogen atom situating at the γ-position may be superimposed with those ascribable to the other hydrogen atoms with a high probability. Furthermore, the carbon atom at the γ-position which never provides any information on the proton is preferably a $^{12}C$ atom. However, the amino acid can be so designed that the γ-position is composed of $^{13}CHD$ and the δ-position is composed of $^{12}CD_2$ so that the chemical shift observed for the carbon atom ($^{13}C$) at the may reflect the cis- or trans-configuration of the peptide bond between the proline residue and the residue just before the same (the residue on the side of the N-terminal).

Thr:

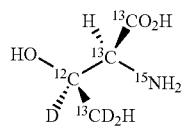

In this amino acid, if taking into consideration the tetrahedral characteristic properties of the carbon atom at the β-position, the methyl group at the γ-position can be replaced with a $^{13}CHD_2$ group and the information on the group can be used as a substitute for the structural information attributable to the signals of the hydrogen atom at the β-position.

When deuterating the hydrogen atom at the β-position, the carbon atom at that position is preferably a $^{12}C$ atom. Conversely, when the methyl group at the γ-position is completely deuterated, the β-position is preferably composed of $^{12}CH$ in order to obtain the structural information useful for the precise determination of the structure.

Val:

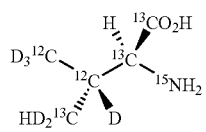

In this amino acid, if taking into consideration the tetrahedral characteristic properties of the carbon atom at the β-position, one of the two methyl groups situating at the γ-position can be stereo-selectively replaced with a $^{13}CHD_2$ group and the other methyl group can be stereo-selectively replaced with a $^{12}CD_3$ group and the structural information on the resulting groups thus obtained can be used as a substitute for the structural information attributable to the signals of the hydrogen atom at the β-position.

When replacing the hydrogen atom at the β-position with a deuterium atom, the carbon atom at that position is preferably a $^{12}C$ atom. Inversely, when simultaneously and completely deuterating the two methyl groups at the γ-position, the β-position is preferably composed of $^{13}CH$ to obtain structural information useful for the precise structure-determination.

The present invention permits the preparation of a target protein composed of stable isotope-labeled amino acids according to the cell-free protein synthesis technique, while making use of the foregoing stable isotope-labeled amino acids as the amino acid components constituting the desired target protein and the present invention likewise permits the subsequent NMR analysis of the resulting target protein to thus elucidate the structure of the protein. In this respect, however, it is preferred to use the foregoing stable isotope-labeled amino acids in combination with the amino acid components disclosed in Patent Document 2 as the aromatic amino acid components which are likewise constituent amino acids of the target protein.

In addition, it is likewise preferred to use amino acid components disclosed in Patent Document 1 as stable isotope-labeled aliphatic amino acids other than the foregoing ones, i.e., arginine (Arg), glutamine (Gln), glutamic acid (Glu), isoleucine (Ile), leucine (Leu), lysine (Lys), methionine (Met), proline (Pro), threonine (Thr) and valine (Val).

Figure 2:
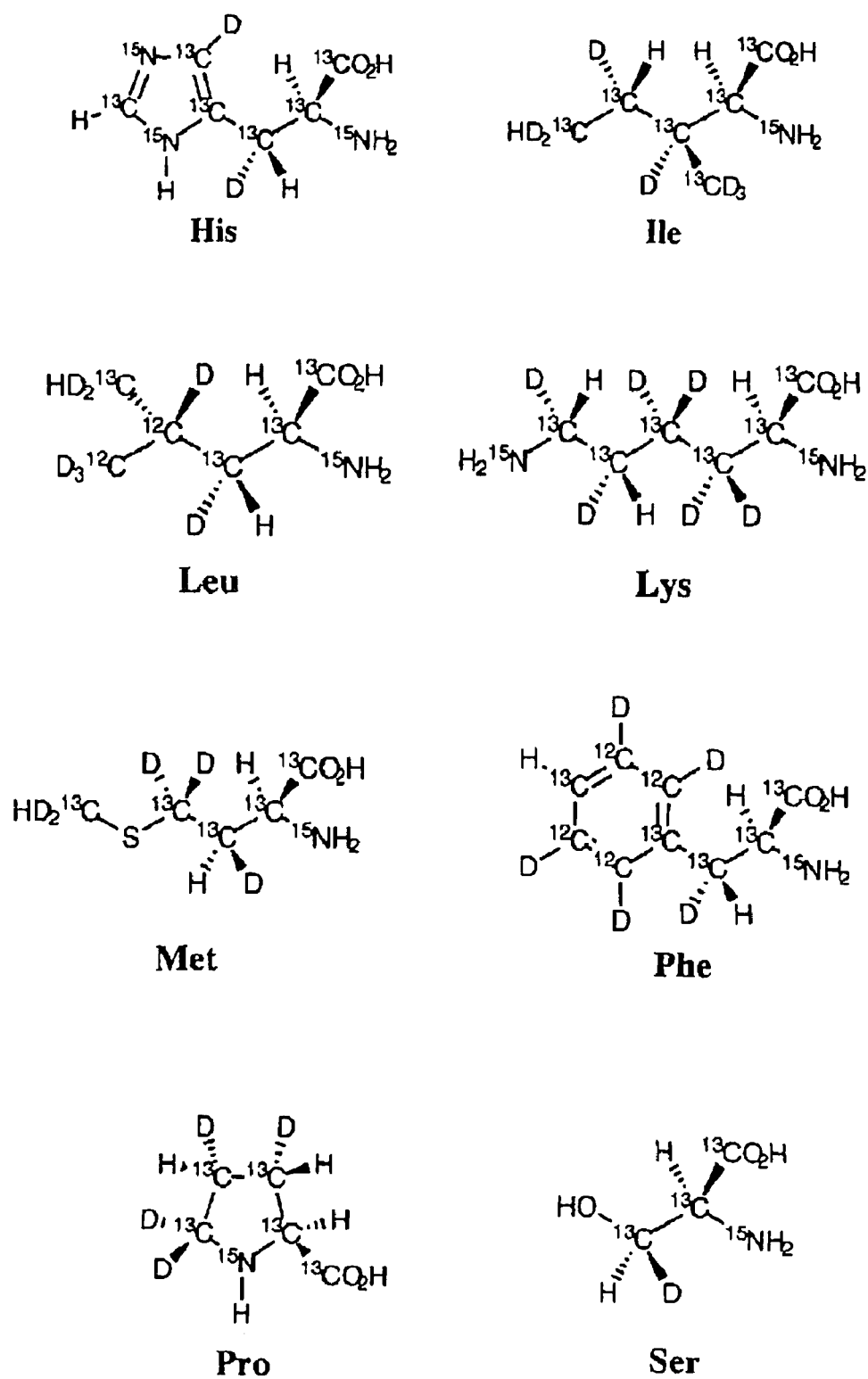

FIG. 2 attached hereto shows the chemical structures of typical stable isotope-labeled amino acids.

To analyze the structure of a protein by the NMR spectrometry, stable isotope-labeled amino acids are incorporated into a target protein. In this respect, arbitrarily selected one, a plurality or the whole of the amino acids constituting a specific target protein can be replaced with the stable isotope-labeled amino acids according to the present invention, each of which has a labelling pattern most efficiently used for obtaining the information on the three-dimensional structure of the target protein like the information discussed herein and for the NMR analysis of the same. In this connection, however, it is preferred that all of the aliphatic amino acids constituting the target protein are replaced with the foregoing stable isotope-labeled aliphatic amino acids of the present invention, while all of the remaining amino acids or all of the aromatic amino acids constituting the target protein are likewise replaced with the foregoing stable isotope-labeled aromatic amino acids. The amino acids constituting the target protein can be replaced with the corresponding stable isotope-labeled amino acids by any conventionally known method such as the usual high expression protein-synthesis system using cultivated biological cells (preferably cell-free protein synthesis system), the organic chemical and/or enzyme-chemical peptide/protein synthesis technique, or the protein synthesis method which makes use of a cell-free extract.

Moreover, the NMR structural analysis of proteins may likewise be carried out according to a variety of techniques. The present invention likewise permits the identification of the site undergoing any structural change caused by the linkage of a ligand.

In any case, the most characteristic properties of the amino acids used in the present invention are such that they have a variety of labelling patterns and therefore, when these amino acids are incorporated into a protein to be analyzed, they would permit the three-dimensional structural analysis of the protein which has never been able to be analyzed by any conventionally known technique.

The present invention permits the design of amino acids optimal for the acquisition of the information on the three-dimensional structure of an intended protein by the use of a combination of the stereo-selective deuteration (SSD) technique, the region-selective deuteration (RSD) technique, the stereo-array deuteration (SAD) technique, the proton-density minimization (PDM) technique and the tailored ring-labelling (TRL) technique, as disclosed in Patent Document 1.

As the NMR structural analysis method of proteins according to the present invention is preferably one for the structural analysis of a target protein, through the NMR measurement, which comprises the step of analyzing the structure of the target protein in which all of the amino acid moieties constituting the same are completely replaced with the aforementioned stable isotope-labeled amino acids.

There will hereunder be illustrated, by way of example, methods for the preparation of a protein labelled with amino acids having various labelling patterns, and various excellent characteristic properties of the NMR spectra observed for the protein, which are useful for obtaining the three-dimensional structure thereof.

It should of course be construed that the following Examples are simply illustrative and given herein for the more particular understanding of the invention of this patent application and accordingly, the present invention is by no means limited to these specific Examples.

EXAMPLES

Example 1

As to Synthetic Methods and Results Obtained in Simulation Experiments

The simulation experiments were herein carried out while taking notice of, in particular, the following viewpoints for the evaluation of the precision and correctness of the structure as has been discussed above:

(1) The estimation of any reduction in the number of NOE observed when the aliphatic amino acids of the present invention are forced to be incorporated into a specific protein;
(2) The effect of any reduction in the quantity of distance information on the precision and correctness of the structure of such a protein;
(3) The influence of any reduction in the number of NOE on the automatic attribution.

In respect of the foregoing viewpoints (1) and (2), the reduction in the number of NOE permitted the direct reduction of any overlapping between signals and made the structural analysis easy, while the distance information necessary for and indispensable to the elucidation of the structure may optionally be lost and therefore, it was essential to investigate the interrelation between the number of NOE and the precision of the structure obtained. Regarding the viewpoint (3), the automatic analytical program CYANA adopts, for the NOE analysis, the algorithm "for carrying out the analysis while relying on the relation between the NOE numbers" (Herrmann T, Guntert P, Wuthrich K., J. Mol. Biol., 2002, 319: 209-227) and, for this reason, it should be confirmed how the automatic analytical algorithm is influenced by any reduction in the NOE numbers (decrease of density) and any reduction in the information on such relationships between the NOE numbers accompanied by the former.

Adopted herein as the model proteins used in the simulation experiments were the following three kinds of proteins: calmodulin (Babu Y S, Bugg C E, Cook W J., J. Mol. Biol., 1988, 204: 191-204), LpxC-deacetylation enzyme (Whittington D A, Rusche K M, Shin H, Fierke C A, Christianson D W., Proc. Natl. Acad. Sci. USA, 2003, 100: 8146-8150), OmpA protein (Pautsch A, Schulz G E., Nat. Struct. Biol., 1998, 5: 1013-1017). Calmodulin is a protein whose structure has already been elucidated with a high precision according to the conventional SAIL technique and it is thus considered to be an optimum model for the investigation of the amino acids of the present invention while comparing them with SAIL amino acids. Therefore, this substance was adopted as a model protein in the simulation experiments. LpxC protein is a protein having the highest molecular weight, among the proteins, in which not less than 90% of the NMR signals have been assigned by the presently used NMR spectroscopy technique (Coggins B E, Li X, McClerren A L, Hindsgaul O, Raetz C R H, Zhou P., Nat. Struct. Biol., 2003, 10: 645-651; and Coggins B E, McClerren A L, Jiang L, Li X, Rudolph J, Hindsgaul O, Raetz C R H, Zhou P., Biochemistry, 2005, 44: 1114-112) and therefore, the data of chemical shifts observed for this protein can be applied to the simulation experiments without any further treatment, and further OmpA protein is, among the membrane proteins, one having a molecular weight falling within the range to which the NMR analysis can be applied. Accordingly, these proteins were used as protein models for the simulative analysis (Arora A, Abildgaard F; Bushweller J H, Tamm L K., Nat. Struct. Biol., 2001, 8: 334-338).

In the practical simulation experiments, each aliphatic amino acid of the present invention was first inspected for the effectiveness in the structural analysis. More specifically, a modified calmodulin obtained by converting only one kind of aliphatic amino acid present in calmodulin to the aliphatic amino acid of the present invention was subjected to the structural analysis-simulation experiment to thus estimate the correlation between the correctness and precision of the protein and the reduced number of NOE. In this calculation, the reduction in the number of NOE was found to be 6 to 216 per one kind of aliphatic amino acid of the present invention and 6 to 21 per one amino acid. As a result, lysine was found to be an amino acid which could most efficiently reduce the number of NOE and, more specifically, it could reduce about 21 NOE signals per single amino acid. On the other hand, these RMSD values were increased by only about 0.01 to 0.08 Å as compared with those obtained according to the conventional SAIL technique. It would be expected that the increase to such an extent can sufficiently be compensated by the effects of making the analysis efficient through the reduction in the overlapping between signals and in the line width of the signal and therefore, the practical experiments would permit the structural analysis at a higher resolution as compared with that achieved by the conventional methods.

Next, simulation experiments were carried out using a model protein in which all of the hydrogen atoms of 19 kinds of amino acids except for glycine were replaced with $^2H$ atoms to examine the effect of amino acids whose rate of deuteration was increased to a level higher than that used in the present invention. As a result, it was found that the RMSD values were considerably higher, in the both correctness and precision, than those observed for the conventional methods. This fact clearly indicates that the both correctness and precision of the structure of a protein would significantly be reduced if the number of $^1H$ atoms in each amino acid component is further reduced to a level smaller than that used in the aliphatic amino acid component of the present invention.

This fact also indicates that the aliphatic amino acid of the present invention is so designed as to have the smallest possible and optimum degree of deuteration.

Figures 2, 3:
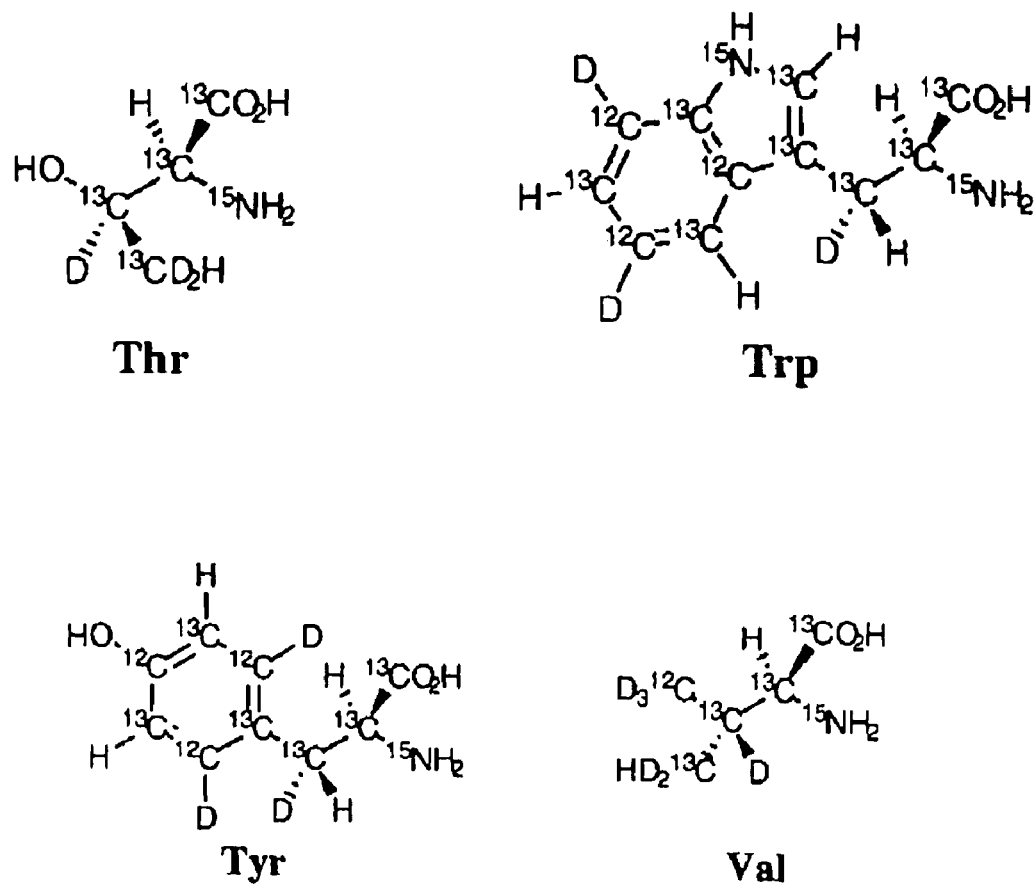
Figure 3:
Figure 3:
Figure 3:
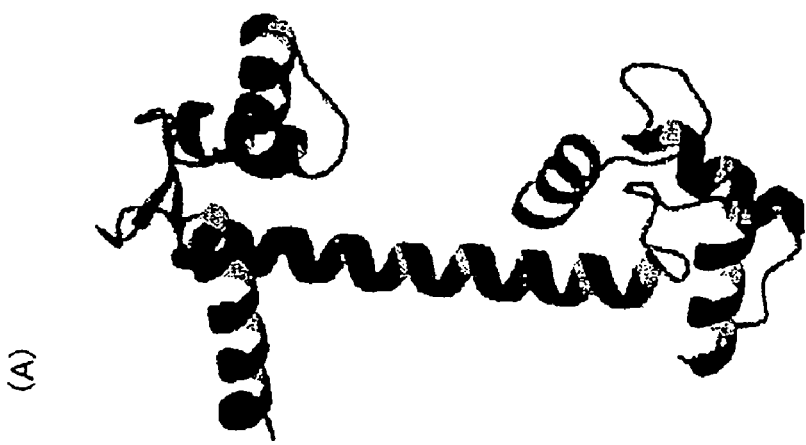
Figure 4:
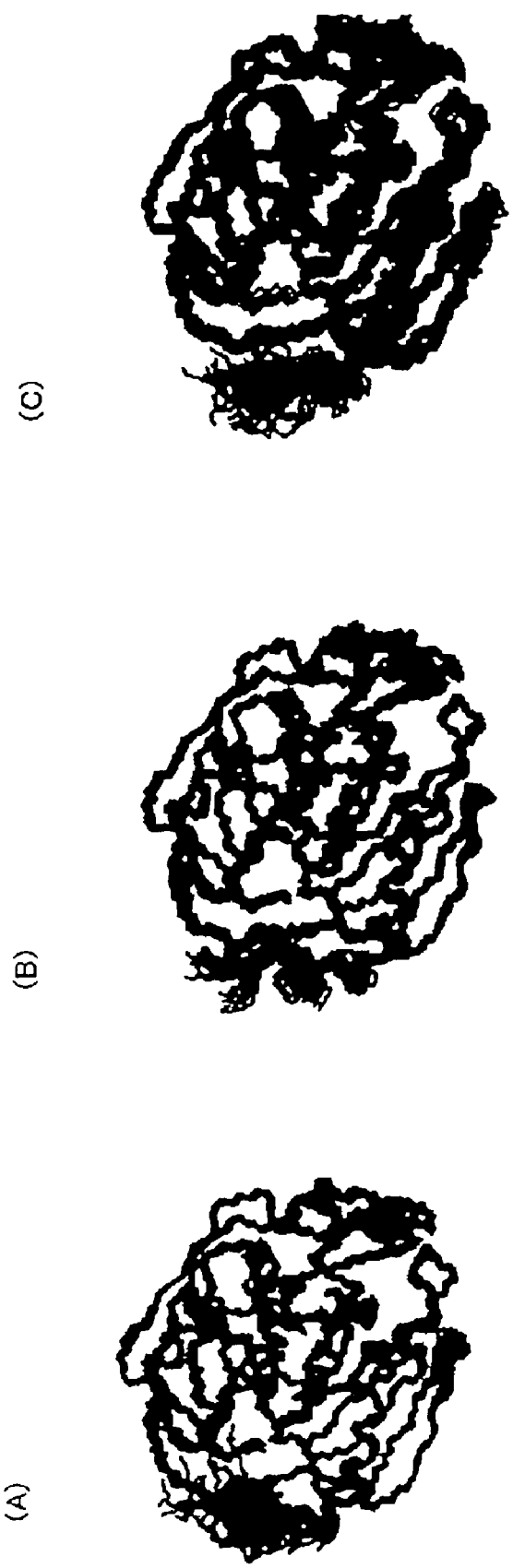
FIG. 4 shows the structures of LpxC protein obtained through the structural elucidation according to the conventional SAIL method (experimental data) or the method of the present invention which makes use of the amino acids of the present invention (data obtained through the simulation experiments). (A): The structure elucidated according to the SAIL method (ribbon model); (B): the structure elucidated according to the SAIL method (bundle model); and (C): the structure elucidated using the amino acids of the present invention.
Figure 5:
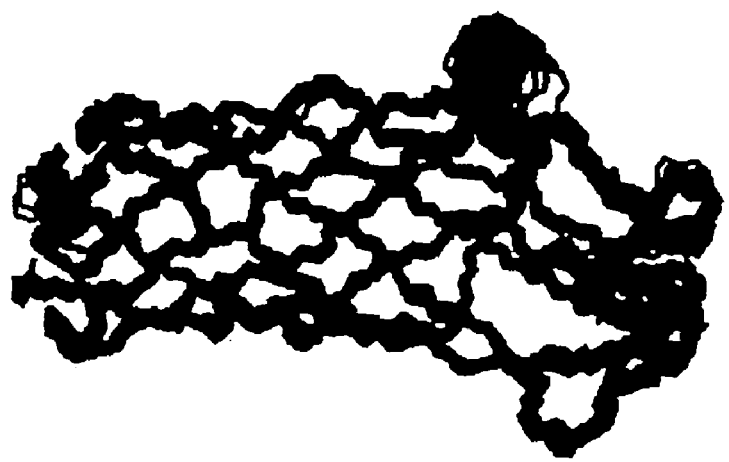
FIG. 5 shows the structures of OmpA protein determined through the structural elucidation according to the conventional SAIL method (experimental data) or the method of the present invention which makes use of the amino acids of the present invention (data obtained through the simulation experiments). (A): The structure elucidated according to the SAIL method (ribbon model); (B): the structure elucidated according to the SAIL method (bundle model); and (C): the structure elucidated using the amino acids of the present invention.
Figure 5:
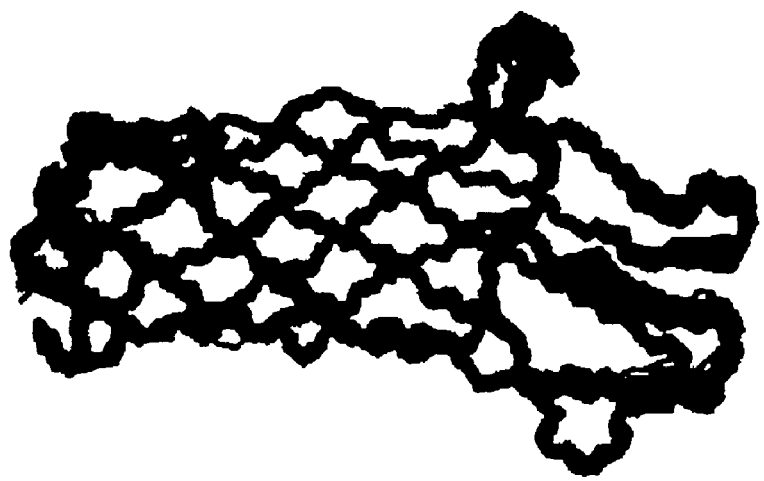
Figure 5:
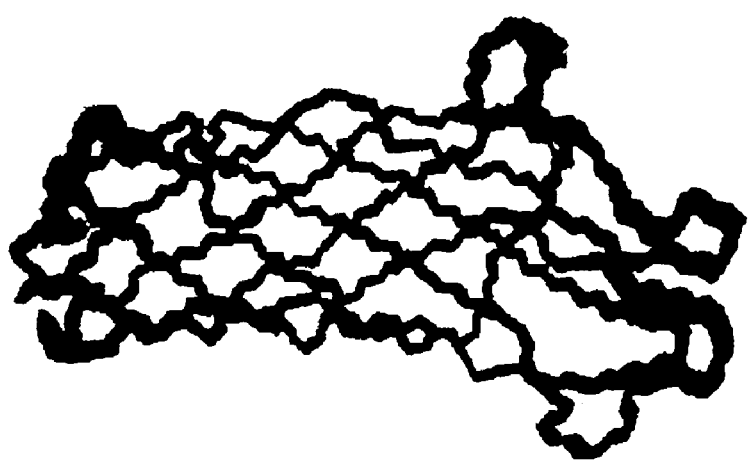

Finally, structural analytical simulation experiments were likewise carried out using calmodulin, LpxC, and OmpA protein, wherein all of the constituent amino acids were replaced with the corresponding stable isotope-labeled aliphatic amino acids (as depicted in FIG. 2). The results thus obtained are summarized in the following Table 1 and the attached FIGS. 3, 4 and 5.

increased as compared with those observed for the conventional techniques, but the numbers of NOE were reduced to a level on the order of almost the half of that observed for the uniformly labelled sample. The degree of convergence observed for the uniformly labelled sample in the simulation experiments was extremely excellent, but it would certainly be presumed that, in the practical experiments, the analysis of a spectral chart including a vast number of signals on the order of, for instance, about 11,000 signals (LpxC) or 9,000 signals (OmpA) is almost impossible because of any possible

TABLE 1

Results obtained in the structural analysis of calmodulin, LpxC, and OmpA protein carried out according to the Uniform Labelling (UL) method, the conventional SAIL method and the method using the amino acids of the present invention:

| | Calmodulin | | | LpxC | | | OmpA | | |
| --- | --- | --- | --- | --- | --- | --- | --- | --- | --- |
| | UL | SAIL | Pre. Inv. | UL | SAIL | Pre. Inv. | UL | SAIL | Pre. Inv. |
| NOESY Peak No. | — | 4814 | 3457 | 11079 | 7615 | 6111 | 8893 | 5435 | 4197 |
| Attributed NOESY Peak No. | — | 4568 | 3159 | 10941 | 7532 | 6036 | 8574 | 5232 | 3941 |
| Main Chain RMSD (Å)$^a$ | — | 0.37 | 0.61 | 0.40 | 0.50 | 0.80 | 0.37 | 0.58 | 0.64 |
| Heavy Atom's RMSD (Å)$^b$ | — | 0.69 | 1.04 | 0.95 | 1.03 | 1.37 | 0.58 | 0.81 | 0.94 |
| Main Chain's RMSD (Å)$^c$ as compared with X-ray | — | 0.95 | 0.87 | 0.89 | 0.95 | 0.97 | 1.01 | 0.94 | 1.24 |

\* Pre. Inv.: Present invention;
$^a$These values were obtained by comparing 20 structures, with one another, outputted by CYANA at the atoms N, C$^α$, C' of the main chain;
$^b$These values were obtained by comparing 20 structures, with one another, outputted by CYANA at the heavy atoms [those extending from 82$^{nd}$ to 146$^{th}$ amino acids (calmodulin); 1$^{st}$ to 255$^{th}$ amino acids (LpxC); and 1$^{st}$ to 172$^{nd}$ amino acids (OmpA)];
$^c$These values were obtained by comparing the average of 20 structures outputted by CYANA with the result obtained through the X-ray crystal structure analysis.

In this connection, CYANA represents software used in the automatic NMR structural analysis (Guntert P., Prog. NMR Spectrosc., 2003, 43: 105-125; Guntert P, Mumenthaler C, Wuthrich K., J. Mol. Biol., 1997, 273: 283-298; Guntert P., Automated NMR structure calculation. In: NMR Techniques in Structural Biology—From Liquid to Solid State, Springer, New York. 2006).

As will be clear from the data listed in Table 1, the RMSD values of the main chains were found to be not more than 1 Å in all of the simulation experiments herein carried out using calmodulin, LpxC, and OmpA protein, in which the aliphatic amino acids of the present invention were used and it was also found that these proteins maintained their structures with a sufficiently high precision. Moreover, even when comparing the RMSD values with the results obtained through the X-ray crystal structure analysis, the results of the simulation experiments obtained using the aliphatic amino acids of the present invention were found to be almost identical to or superior to those obtained in the conventional SAOL method. Regarding the degree of convergence, the RMSD values were slightly overlapping between such signals. On the other hand, it would be believed that a slight reduction of the precision in the structural analysis due to the use of the aliphatic amino acids of the present invention can sufficiently be compensated by making the structural analysis more efficient through the reduction in the number of NOE. Further, in respect of the influence of the NOE density reduction on the automatic structural analysis, it was demonstrated that a target protein could still sufficiently be used for the automatic structural analysis inasmuch as the number of $^1$H atoms included in the amino acids or the target protein was simply reduced to a level corresponding to those observed for the amino acids of the present invention, since the automatic analytical program CYANA could automatically attribute 94 to 96% of the total NOE.

Then the following Table 2 shows the statistical structural data observed when only one kind of amino acid component included in the SAIL calmodulin were replaced with the corresponding amino acid of the present invention:

TABLE 2

| | SAIL | ARG | HIS | ILE | LEU | LYS | MET |
| --- | --- | --- | --- | --- | --- | --- | --- |
| NOESY Peak No. | 4814 | 4738 | 4808 | 4681 | 4692 | 4647 | 4710 |
| Attributed NOESY Peak No. | 4568 | 4487 | 4567 | 4428 | 4440 | 4400 | 4459 |
| Main Chain RMSD (Å)$^a$ | 0.37 | 0.44 | 0.40 | 0.43 | 0.42 | 0.39 | 0.44 |
| Heavy Atom's RMSD (Å)$^b$ | 0.69 | 0.79 | 0.72 | 0.74 | 0.76 | 0.74 | 0.76 |
| Main Chain's RMSD (Å)$^c$ as compared with X-ray | 0.95 | 1.08 | 0.95 | 1.00 | 1.06 | 0.97 | 0.94 |

| | PRO | PHE | THR | VAL | GLN | GLU | noH$^α$ |
| --- | --- | --- | --- | --- | --- | --- | --- |
| NOESY Peak No. | 4777 | 4665 | 4698 | 4700 | 4719 | 4598 | 3030 |
| Attributed NOESY Peak No. | 4521 | 4411 | 4446 | 4451 | 4493 | 4336 | 2724 |
| Main Chain RMSD (Å)$^a$ | 0.41 | 0.38 | 0.40 | 0.42 | 0.45 | 0.41 | 0.92 |

TABLE 2-continued

| | | | | | | | |
|---|---|---|---|---|---|---|---|
| Heavy Atom's RMSD (Å)[b] | 0.72 | 0.46 | 0.73 | 0.75 | 0.78 | 0.80 | 1.38 |
| Main Chain's RMSD (Å)[c] as compared with X-ray | 1.08 | 1.03 | 1.00 | 0.88 | 0.89 | 0.93 | 1.31 |

[a]These values were obtained by comparing 20 structures, with one another, outputted by CYANA at the atoms N, C$^\alpha$, C' of the main chain;
[b]These values were obtained by comparing 20 structures, with one another, outputted by CYANA at the heavy atoms [those extending from 82$^{nd}$ to 146$^{th}$ amino acids (calmodulin); 1$^{st}$ to 255$^{th}$ amino acids (LpxC); and 1$^{st}$ to 172$^{nd}$ amino acids (OmpA)];
[c]These values were obtained by comparing the average of 20 structures outputted by CYANA with the result obtained through the X-ray crystal structure analysis.

From the viewpoints discussed above or from the conclusion deduced from the results obtained in the foregoing simulation experiments, each of the amino acids according to the present invention is so designed to realize the deuteration of a target protein optimum for the determination or elucidation of the structure thereof and the foregoing results likewise sufficiently suggest that an automatic analysis system may be applied to the structural elucidation of a protein correctively and highly precisely even when the amino acids of the invention are applied to extremely high molecular weight proteins or membrane proteins.

Synthesis of Isotope-Labeled Amino Acid

It is thus proved, from the results obtained in the foregoing simulation experiments, that the isotope-labeled aliphatic amino acids herein disclosed can suitably be applied to extremely high molecular weight proteins or membrane proteins for the elucidation of the structure thereof and accordingly, the following isotope-labeled amino acids were actually prepared. The compounds thus prepared each were assigned by the confirmation of the fact that the signals to be ascribed to the deuterated sites were disappeared (this was confirmed by the use of the $^1$H NMR spectroscopy) and the fact that the carbon nuclei undergoing isotope shifts due to the deuteration caused coupling with $^2$H atoms (this was confirmed according to the $^{13}$C NMR spectroscopy).

Example 2

Synthesis of Glutamic Acid (2S,3S,4R)-[1,2,3,4,5-13C5;2-15N;3,4-2H2] Glutamic acid derived from L-glutamic acid uniformly labelled with $^{13}$C atoms according to the method disclosed in an article (M. Oba et al., J. Org. Chem., 1999, 64: 9275) was heated in deuterated hydrochloric acid to thus give (2S,3S)-[1,2,3,4,5-13C5;2-15N;3,4,4-2H3] glutamic acid.

Example 3

Preparation of Lysine (2S,5S,6R)-[1,2,3,4,5,6-13C6;2,6-15N2;3,4,4,5,5,6-2H6] Lysine was synthesized according to the method as disclosed in PCT/JP02/13303 using (2S,3S)-[1,2,3,4,5-13C5;2-15N;3,4,4-2H3] glutamic acid. In this respect, deuterium gas was used when catalytically hydrogenating dehydro-histidine, the resulting (2S,5S,6R)-[1,2,3,4,5,6-13C6;2,6-15N2;2,3,3,4,4,5,6-2H7] lysine was converted into the racemic isomer thereof in light water followed by the optical resolution of the racemic body to thus give the desired product. In addition, the lysine corresponding to [Chemical Formula 8] can likewise be prepared according to the same procedures using [1,2,3,4,5-13C5;2-15N;3,4-2H] glutamic acid, as a starting material.

Example 4

Synthesis of Leucine (2S,3S,4S)-[1,2,3,4,5-13C5;2-15N;3,4,5,5,5',5',5'-2H6] Leucine was synthesized while referring to the description of PCT/JP02/13303 and an article (M. Oba et al., J. Org. Chem., 1999, 64: 9275).

Example 5

Synthesis of Methionine (2S,3R)-[1,2,3,4,6-13C5;2-15N;3,4,4,6,6-2H4] Methionine was synthesized by first converting into its SMe derivative according to the method as disclosed in PCT/JP02/13303 without subjecting the terminal aldehyde group to any asymmetric reduction.

Example 6

Synthesis of Proline

The desired proline was derived from uniformly 13C- and 15N-labelled L-glutamic acid according to the procedures disclosed in an article (M. Oba et al., J. Org. Chem., 1999, 64: 9275-9278), while all of the asymmetric reduction steps of the δ-position were carried out using deuterated reagents. In addition, the proline corresponding to [Chemical Formula 10] can likewise be prepared according to the same procedures, while making use of (2S,3S)-[1,2,3,4,5-13C5;2-15N;3,4,4-2H3] glutamic acid, as a starting material.

Example 7

Synthesis of Arginine (2S,4S,5R)-[1,2,3,4,5-13C5;2,6-15N2;3,3,4,5-2H4] Arginine was synthesized according to the method as disclosed in PCT/JP02/13303 using (2S,3S)-[1,2,3,4,5-13C5;2-15N;3,3-2H2] glutamic acid as a starting material. Moreover, the arginine corresponding to [Chemical Formula 1] can likewise be prepared according to the same procedures while making use of [1,2,3,4,5-13C5;2-15N;2,3,3,4,4-2H5] glutamic acid, as a starting material.

Example 8

Synthesis of Glutamine (2S,3S)-[1,2,3,4,5-13C5;2-15N;3,4,4-2H3] Glutamine was synthesized according to the method as disclosed in PCT/JP02/13303 using (2S,3S)-[1,2,3,4,5-13C5;2-15N; 3,4,4-2H3] glutamic acid as a starting material.

Example 9
Isoleucine
Isoleucine was synthesized according to the following reaction scheme. In this connection, the compound 5 serving as a key compound to the synthesis of this amino acid was synthesized while referring to the disclosure of an article (Eur. J. Org. Chem., 2003, pp. 4664-4678).
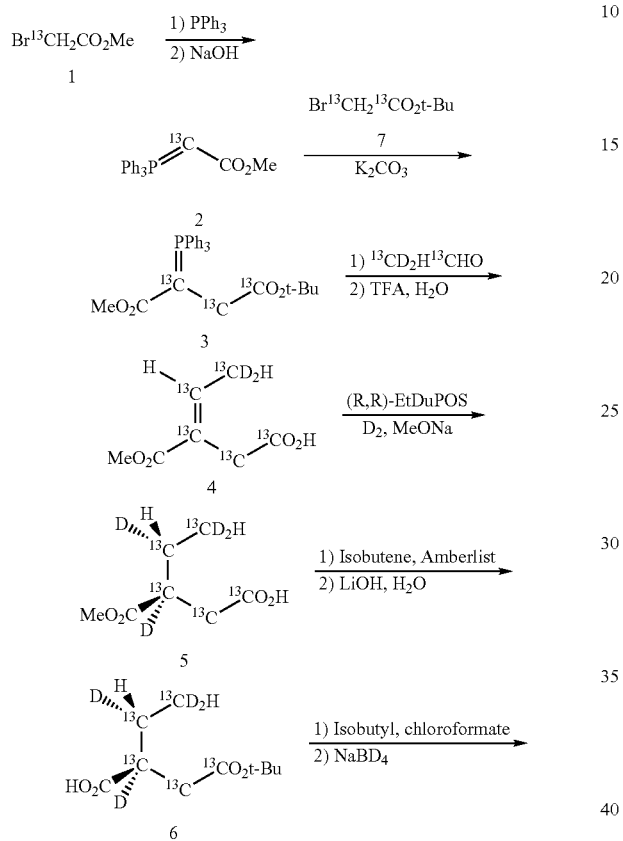
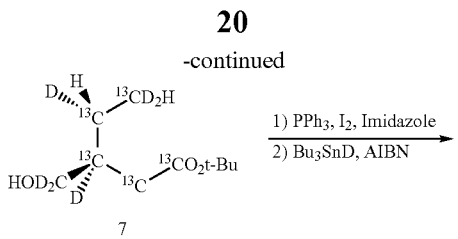
Example 10
Threonine
Threonine was synthesized according to the following reaction scheme:
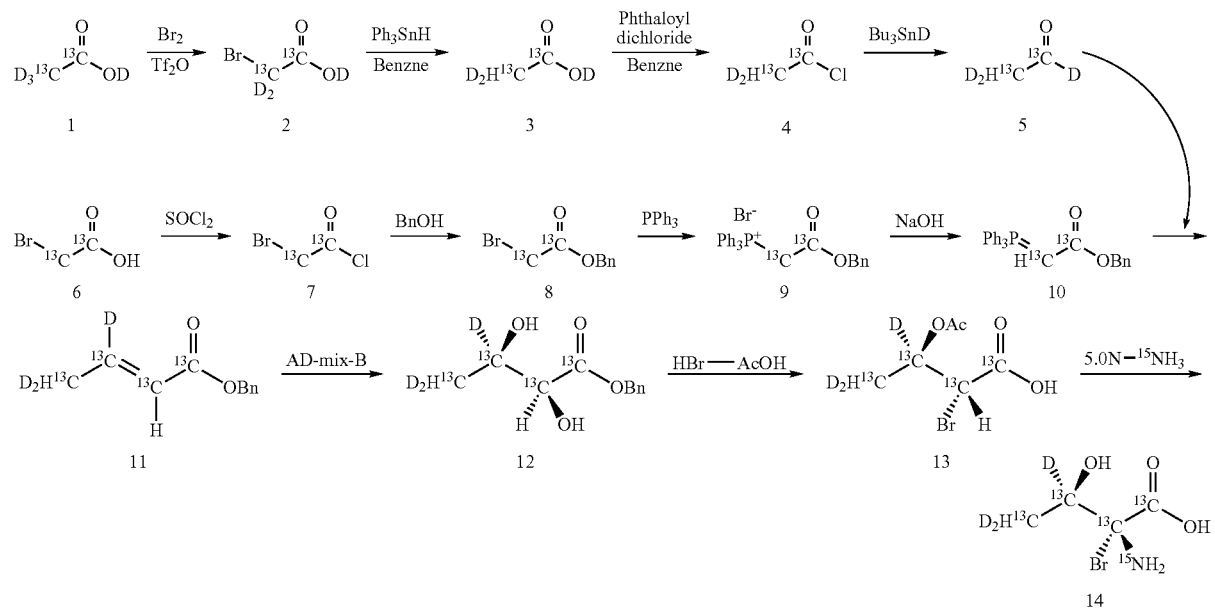

Example 11

Valine

Valine was synthesized according to the reaction scheme given below. In this connection, the compound 7 serving as a key compound to the synthesis of this amino acid was synthesized while referring to the disclosure of an article (Eur. J. Org. Chem., 2003, pp. 4664-4678).

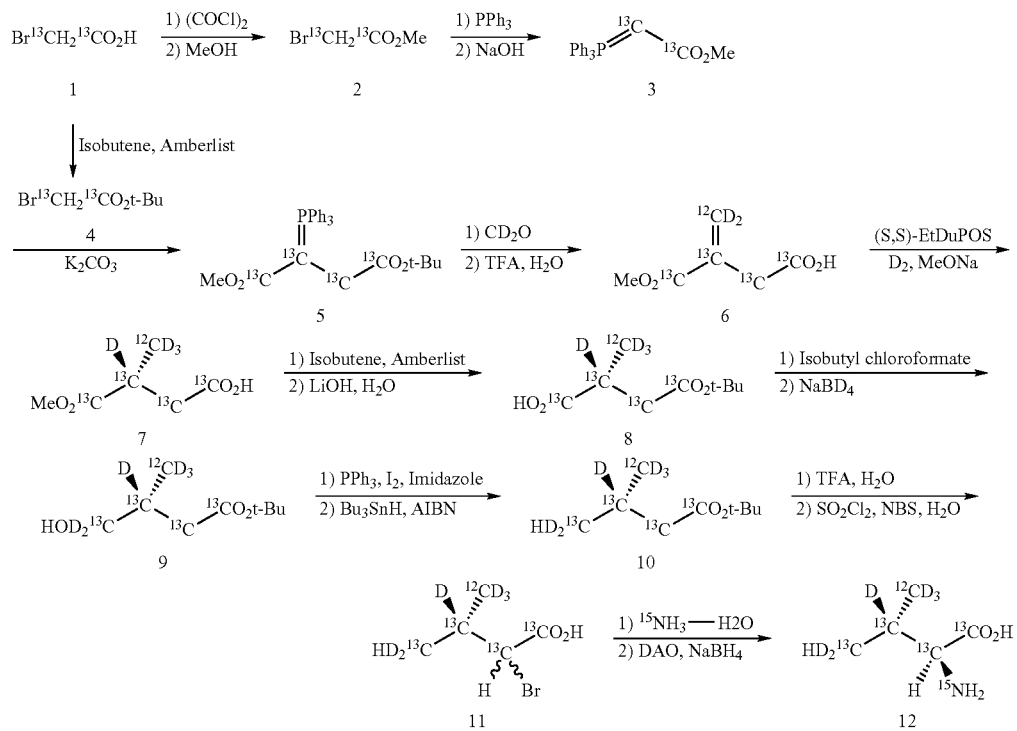

Each of the isotope-labeled aliphatic amino acids synthesized according to the foregoing methods has the structure given below:

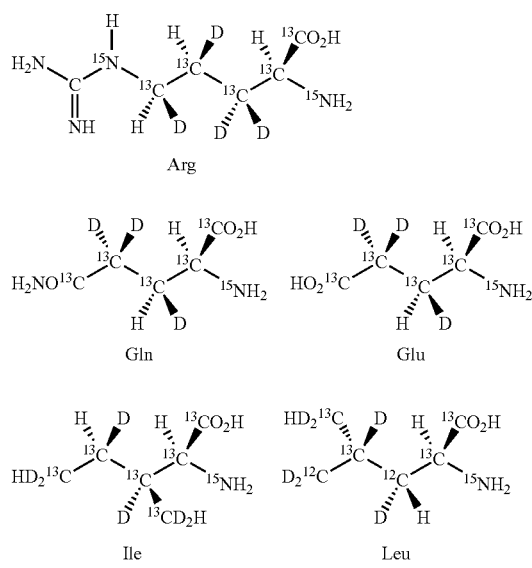

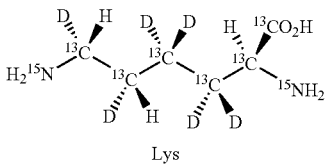

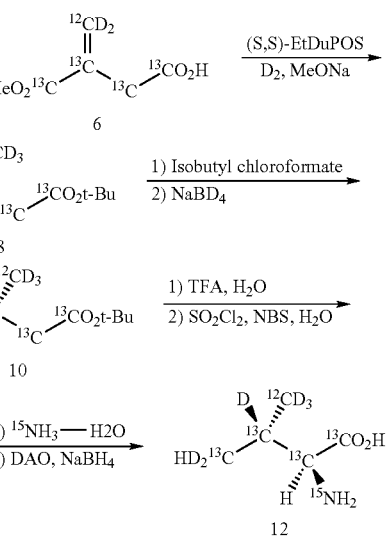

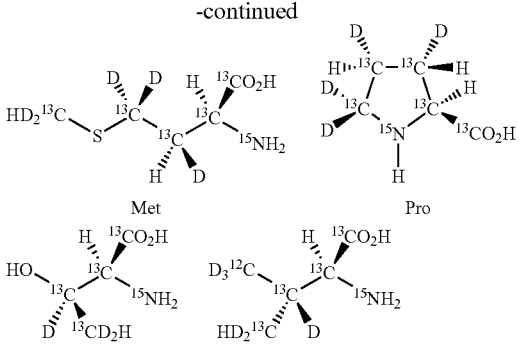

What is claimed is:
1. A composition of stable isotope-labeled amino acids wherein all of the aliphatic amino acids constituting a target protein satisfy the following requirements concerning the labeling pattern:
   (a) When only one methylene group carrying two hydrogen atoms exists, one of the methylene hydrogen atoms is deuterated;
   (b) When at least two methylene groups each carrying two hydrogen atoms exist, one of the methylene hydrogen atoms of at least one of the methylene groups is deuterated and the both of the two methylene hydrogen atoms of at least one of the methylene groups are likewise deuterated;

(c) When pro-chiral gem-methyl groups exist, all of the hydrogen atoms on one of the methyl groups are completely deuterated while the hydrogen atoms on the other methyl groups are partially deuterated;

(d) When a further methyl group in addition to the foregoing ones exists, the methyl group is partially deuterated, or the methyl group is completely deuterated; and (e) side chain methine hydrogen atoms are deuterated;

wherein the aliphatic amino acids are selected from the group consisting of arginine, glutamine, glutamic acid, isoleucine, leucine, lysine, methionine, proline, threonine and valine; and wherein the isotope is selected from carbon, hydrogen, and nitrogen.

2. A composition of stable isotope-labeled amino acids in which arginine (Arg), glutamine (Gln), glutamic acid (Glu), lysine (Lys), methionine (Met) and proline (Pro) constituting a target protein satisfy the following requirements concerning the labeling pattern:

(b) one of the methylene hydrogen atoms of at least one of the methylene groups is deuterated and the both of the two methylene hydrogen atoms of at least one of the methylene groups are likewise deuterated; and (d) when they each have a methyl group, the methyl group is partially deuterated, or the methyl group is completely deuterated; and wherein the isotope is selected from carbon, hydrogen, and nitrogen.

3. The composition of stable isotope-labeled amino acids as set forth in claim 1, wherein (f) after the deuteration, all of the carbon atoms of methylene groups and/or methyl groups each carrying hydrogen atoms are replaced with $^{13}C$ atoms.

4. The composition of stable isotope-labeled amino acids as set forth in claim 1, wherein (g) the carbon atoms of the completely deuterated methylene groups are replaced with 13C and/or 12C.

5. The composition of stable isotope-labeled amino acids as set forth in claim 1, wherein (h) the carbon atoms of the completely deuterated methylene groups are replaced with 12C.

6. The composition of stable isotope-labeled amino acids as set forth in claim 2, wherein all of the carbon atoms present in the amino acids are 13C atoms.

7. The composition of stable isotope-labeled amino acids as set forth in claim 2, wherein one of the hydrogen atoms present on the methylene group at β-position is deuterated.

8. The composition of stable isotope-labeled amino acids as set forth in claim 1, wherein the amino acid in which one methylene group carrying two hydrogen atom is present or which is free of any such a methylene group is isoleucine (Ile), valine (Val), threonine (Thr), or leucine (Leu) and the methine groups situating at the β-positions of isoleucine (Ile) and valine (Val) and that situating at γ-position of leucine (Leu) are deuterated.

9. The composition of stable isotope-labeled amino acids as set forth in claim 1, wherein the carbon atoms of the methine groups situating at the β-positions of isoleucine (Ile), valine (Val) and threonine (Thr) and that situating at γ-position of leucine (Leu) are 12C atoms.

10. The composition of stable isotope-labeled amino acids as set forth in claim 1, wherein the nitrogen atoms constituting the amino acids are completely or partially replaced with 15N.

11. The composition of stable isotope-labeled amino acids as set forth in claim 1, wherein the isotope-labeled amino acids are those represented by the following formulas (1) to (13):

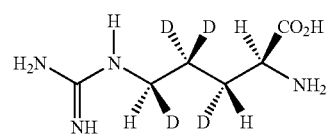

[Chemical Formula 1]

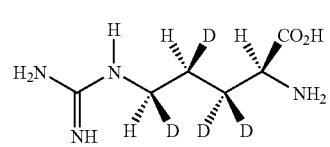

[Chemical Formula 2]

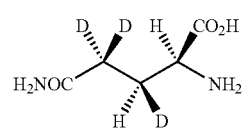

[Chemical Formula 3]

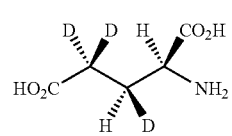

[Chemical Formula 4]

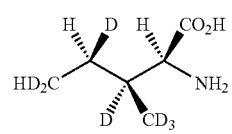

[Chemical Formula 5]

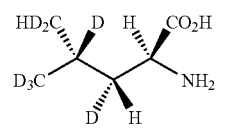

[Chemical Formula 6]

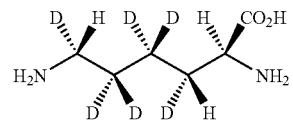

[Chemical Formula 7]

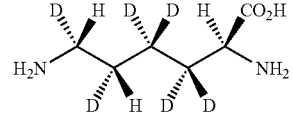

[Chemical Formula 8]

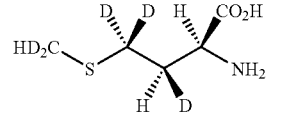

[Chemical Formula 9]

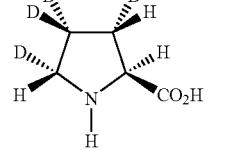

[Chemical Formula 10]

-continued

[Chemical Formula 11]

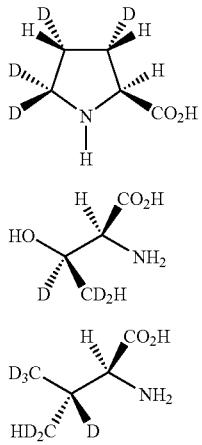

[Chemical Formula 12]

[Chemical Formula 13]

wherein, in these formulas, the carbon atoms are $^{12}$C or $^{13}$C atoms; the nitrogen atoms are $^{14}$N or $^{15}$N atoms; H represents a hydrogen atom; and D represents a deuterium atom.

12. A composition of stable isotope-labeled amino acids constituting a target protein wherein the aliphatic amino acids constituting the target protein are stable isotope-labeled aliphatic amino acids as set forth in claim 1 and wherein the aromatic amino acids constituting the target protein are selected from following stable isotope-labeled aromatic amino acids:

A stable isotope-labeled phenylalanine, in which the carbon atom of a phenyl group attached to an amino acid residue represented by the following formula A is $^{13}$C atom; 2 to 4 carbon atoms out of the remaining 5 carbon atoms constituting the phenyl group are $^{12}$C atoms, each of which is combined with a deuterium atom; and the remaining carbon atoms of the phenyl group are $^{13}$C atoms, each of which is combined with a hydrogen atom;

A stable isotope-labeled tyrosine, in which the carbon atom of a phenyl group attached to an amino acid residue represented by the following formula A is $^{13}$C atom; the carbon atom combined with the hydroxyl group (OH group) present on the phenyl group is a $^{12}$C atom or a $^{13}$C atom; 2 to 4 carbon atoms out of the remaining 4 carbon atoms constituting the phenyl group are $^{12}$C atoms, each of which is combined with a deuterium atom; and the remaining carbon atoms of the phenyl group are $^{13}$C atoms, each of which is combined with a hydrogen atom;

A stable isotope-labeled tryptophane, in which the carbon atom of an indolyl group attached to an amino acid residue represented by the following formula A is $^{13}$C atom; 1 to 5 carbon atoms out of the remaining 7 carbon atoms constituting the indolyl group are $^{12}$C atoms, each of which is combined with a deuterium atom; the remaining carbon atoms of the indolyl group are $^{13}$C atoms, each of which is combined with a hydrogen atom; and the nitrogen atom of the NH group constituting the indolyl group is a $^{15}$N atom or a $^{14}$N atom; and A stable isotope-labeled histidine, in which the carbon atom of an imidazolyl group attached to an amino acid residue represented by the following formula A is $^{13}$C atom; the both of the remaining 2 carbon atoms constituting the imidazolyl group are $^{13}$C atoms, which are each combined with a hydrogen atom, or one of the carbon atoms is a $^{13}$C atom which is combined with a deuterium atom and the other carbon atom is a $^{13}$C atom which is combined with a hydrogen atom; one of the two nitrogen atoms constituting the imidazolyl group is a $^{15}$N atom and the other thereof is a $^{14}$N atom; and the hydrogen atom constituting the NH group is not a deuterium atom:

$$—*^1C(X)(Y)—*^2C(Z)(^{15}NH)(*^3COOH) \quad (A)$$

wherein each of $*^1C$, $*^2C$, and $*^3C$ represents $^{12}$C or $^{13}$C; X, Y and Z each represent a hydrogen atom or a deuterium atom.

* * * * *